(12) United States Patent
Adachi et al.

(10) Patent No.: US 6,498,007 B1
(45) Date of Patent: Dec. 24, 2002

(54) METHODS OF TREATMENT OF DISEASE USING ADSORBENT CARRIERS

(75) Inventors: Masakazu Adachi, Takasaki (JP); Toshifumi Hibi, Tokyo (JP)

(73) Assignee: Japan Immunoresearch Laboratories Co., Ltd., Gumma (JP)

( * ) Notice: Subject to any disclaimer, the term of this patent is extended or adjusted under 35 U.S.C. 154(b) by 0 days.

(21) Appl. No.: 09/700,632
(22) PCT Filed: Feb. 25, 2000
(86) PCT No.: PCT/JP00/01099
§ 371 (c)(1), (2), (4) Date: Nov. 17, 2000
(87) PCT Pub. No.: WO00/55621
PCT Pub. Date: Sep. 21, 2000

(30) Foreign Application Priority Data

Mar. 17, 1999 (JP) .............................. 11-072144
Aug. 18, 1999 (GB) ................................. 9919565

(51) Int. Cl.[7] ...................... A61M 37/00; A61K 39/21; C12Q 1/70
(52) U.S. Cl. .................. 435/5; 604/4.01; 604/5.01; 604/5.02; 604/6.01; 604/6.03; 424/208.1; 424/228.1; 424/248.1; 422/101; 210/435; 210/90; 210/263; 210/502.1; 210/500.3; 210/645
(58) Field of Search .............. 424/208.1, 228.1, 424/248.1; 210/435, 90, 263, 502.1, 500.3, 645; 422/101; 604/4.01, 5.01, 5.02, 6.01, 6.03; 435/5

(56) References Cited

U.S. PATENT DOCUMENTS

| | | | |
|---|---|---|---|
| 4,906,742 A | * 3/1990 | Young et al. | ................. 536/27 |
| 5,403,719 A | 4/1995 | Adachi et al. | ................ 435/29 |
| 5,567,443 A | 10/1996 | Kashiwagi et al. | ......... 424/529 |
| 5,593,586 A | 1/1997 | Yamazaki et al. | ......... 210/435 |
| 5,725,768 A | 3/1998 | Adachi et al. | ............. 210/435 |

FOREIGN PATENT DOCUMENTS

WO 9609068 3/1996 .......... A61K/31/40

OTHER PUBLICATIONS

Zignego et al., Hepatitis C virus infection of mononuclear cells from peripheral blood and liver infiltrates in chronically infected patients, Journal of Medical Virology, 47:58–64 (1995).*
International Search Report.
Bruisten, S.M., et al., "Efficiency of white cell filtration and a freeze-thaw procedure for removal of HIV-infected cells from blood", Transfusion, vol. 30, No. 9, 1990, pp. 833–837.

* cited by examiner

Primary Examiner—Hankyel T. Park
Assistant Examiner—Stacy S. Brown
(74) Attorney, Agent, or Firm—Sughrue Mion, PLLC

(57) ABSTRACT

The invention relates to a method for the removal of leucocytes from blood which comprises bringing blood that comprises infected leucocytes into contact with an adsorbent carrier that has a greater affinity for infected, activated and/or defective leucocytes than for uninfected leucocytes especially cellulose acetate. The method can be used in the apheresis treatment of diseases caused by pathogenic organisms, for example, HIV, HCV or malaria. It is especially useful for treatment of HIV.

36 Claims, 14 Drawing Sheets

METHODS OF TREATMENT OF DISEASE USING ADSORBENT CARRIERS

TECHNICAL FIELD

This invention relates to a method involving blood leucocyte apheresis for treatment of disease.

BACKGROUND ART

For some time, therapeutic apheresis has been known as an alternative strategy for the management of disorders. The technique involves the removal of cells or proteins that are implicated in the pathogenesis of the disorder, for example rheumatoid factor, immune complexes and other humoral mediators in the plasma (1, 2). Procedures employing selective removal of blood cells or plasma components, without the use of replacement fluids, are associated with minimal side effects (1). An outpatient approach is possible, which is more convenient for the patient and reduces the cost of the procedure (2). Many of the unacceptable side-effects of chronic drug therapy are also reduced by use of the technique.

In EP-A-0-319961 there is described a method for the selective removal of granulocytes from blood by bringing the blood into contact with an adsorbent carrier having a higher affinity for granulocytes than for lymphocytes. That invention is concerned with cancer treatment. An apparatus for carrying out the method is also described in that application. A similar apparatus is described in U.S. Pat. No. 5,725,768.

In JP 0193 481 and U.S. Pat. No. 5,567,443 there is described a method for the treatment of inflammatory disease which comprises bringing blood from a patient into contact with an adsorbent carrier that has an affinity for inflammatory cells (granulocytes and monocytes) which is greater than its affinity for lymphocytes. The method is reported to be useful for treating acute respiratory distress syndrome, rheumatoid arthritis, autoimmune diseases, allergic diseases and reflow disorders following myocardial infarction.

AIDS is a life-threatening immunodeficiency condition caused by HIV (human immunodeficiency virus). After confirmation and onset of HIV infection, the mortality rate is very high. No effective treatment strategy has been established yet for the treatment of AIDS and, owing to a long latent period, it is also difficult to establish an effective measure for the prevention of infection.

After infection with HIV, anti-HIV antibody appears in the blood, generally within 6 to 8 weeks. Deficiency of or disturbance to the immune system proceeds, leading eventually to AIDS. For convenience, the intermediate stage is classified as AIDS related complex (ARC). Certain cells infected with HIV harbour the virus and act as reservoirs of the HIV. Such cells include mononuclear cells (monocytes/macrophages) and resting CD4$^+$ lymphocytes. While the virus is inside those cells, it is protected from clearance by the immune system. The virus is also shielded from contact with administered drugs so effective treatment of the condition is thus difficult.

The main symptoms of AIDS include fever, persistent systemic lymphadenoma, weight loss (cachexia) and diarrhoea. In addition, opportunistic infectious diseases and malignant tumours may develop and profoundly aggravate the patient's condition. Neuropathy may also become a serious problem and, depending on the patient, a disease of the cranial nervous system may also appear.

Based on an immunological consideration of full blown HIV-induced disease (AIDS), the condition is characterised by a profound impairment of the immune response, including decline in CD4$^+$ T lymphocytes, dysregulated cytokine production, increased production of proinflammatory or immunosuppressive cytokines such as TNF-$\alpha$, IL-1$\beta$, IL-6 and IL-10 by peripheral blood cells (3–6) including monocytes (3) and also by granulocytes (4) and enhanced susceptibility of immune cells to apoptosis. HIV antigens such as gp120 bound to immune complexes are believed to induce apoptosis of CD4$^+$ cells (7–12). TNF-$\alpha$, IL-1$\beta$, IL-6 are reported to promote HIV replication (3). At the same time, there is a profound impairment of the ability of monocytes from HIV-infected patients to generate IL-12 (an immunoregulator cytokine). Thus, in healthy individuals, monocytes mainly produce IL-12, whereas in HIV-infected individuals, monocytes produce mainly IL-10. IL-10 was shown to have a pivotal role in the aforementioned changes in the production of cytokines (5, 6). In this context, it is also important to indicate that IL-2 and IL-12 reduce, whereas IL-10 increases susceptibility of CD4$^+$ cells of HIV-infected patients to apoptosis (13–17).

Currently, the treatment strategy for HIV infection consists primarily of highly active antiretroviral drug therapy (HAART) which includes a protease inhibitor. However, whilst in some patients, HAART has been shown to increase CD4$^+$ cell count and to suppress plasma HIV viral load to undetectable levels, as yet no drug treatment is known to affect cellular reservoirs of HIV, for example, in cells including mononuclear cells (monocytes/macrophages) and resting CD4$^+$ lymphocytes. These cells serve as sites for an HIV reservoir and as sites for HIV replication and dissemination. This means that when drug treatment is ceased, there is a very strong possibility of relapse attributable to HIV propagation from the aforementioned reservoir cells and de navo infection. In the light of this understanding and for complete eradication of HIV, it is considered to be essential to eliminate the infected resting cells (latent HIV reservoirs). However, at present, there is no drug that can affect the cellular HIV reservoirs, the HIV-1 proviral DNA load in the latently infected mononuclear cells (monocytes/macrophages) and resting CD4$^+$ lymphocytes.

The hepatitis C virus (HCV) infects cells, for example liver cells, and subsequently harbours in those cells and in leucocytes during an apparently latent period. At present, there is no drug that can affect the cellular HCV reservoirs in those latently infected cells.

*Mycobacterium leprae* infects and then remains in mononuclear cells. Present drug treatments are largely ineffective against the organism when inside the cells.

The present invention is based on the surprising observation that leucocytes infected with HIV can be selectively removed from blood.

DISCLOSURE OF INVENTION

The present invention provides a method for the removal of infected, activated and/or defective leucocytes from blood, which comprises bringing blood that comprises infected, activated and/or defective leucocytes into contact with an adsorbent carrier that has a greater affinity for infected, activated and/or defective leucocytes than for uninfected, non-activated or non-defective leucocytes. If desired, the treated blood may be returned to the subject from whom it was obtained.

The method of the present invention effects selective adsorption of infected, defective and activated leucocytes including mononuclear cells i.e. monocytes/macrophages, and also activated lymphocytes, for example CD4+ lymphocytes, including resting CD4+ lymphocytes. Normal, that is to say, non-infected, non-activated and non-defective leucocytes do not appear to adhere to the adsorbent carrier. This is surprising, as the previous uses of apheresis were based on the fact that granulocytes or inflammatory cells, classified as granulocytes and monocytes, were selectively adsorbed in preference to lymphocytes. Contrary to the previous observations that selective adsorption is based on cell type, we have now found that infection of a leucocyte with a virus, which is an intracellular parasite, activation of a leucocyte and/or defects in a leucocyte brings about adsorption to an apheresis column regardless of the leucocyte type.

We presently believe that infection results in selective binding of a population of leucocytes to an adsorbent carrier. We believe that this is owing to a change in a property of the leucocytes, for example a change in the cell surface receptor population, for example a change in receptor types or receptor numbers. A change caused to a leucocyte by infection may be considered as activation of the leucocyte, or the leucocyte may be regarded as defective. However, leucocytes may be activated or rendered defective in other ways that result in the same or analogous selective binding as does infection. Infection, activation and/or defects may result in the same or similar cell surface changes, for example the changes may be in the same receptor type. However, this may not be the case, and the method of the invention is not dependant on the precise mechanism of the selective adsorption of the infected, activated and/or defective leucocytes.

Whilst the aforementioned is the current theory for the functioning of the invention, the applicant is not bound by this theory.

In a further embodiment of the invention immune recovery in a patient infected with a pathogenic organism is effected by contacting blood from the patient with a carrier having a contact angle to water within the range of from 55° to 95° and returning the blood to the patient. The absorbent carrier may be as described above, and is preferably cellulose acetate, especially in one of the preferred forms described above.

When the method of the invention is carried out, the above described effects relating to leucocyte removal and the immune recovery both occur.

Immune recovery denotes an improvement in any one or more aspects of the immune system. One aspect of immune recovery is an immunological improvement. HIV has a particularly profound effect on a subject's immune system.

Another aspect of immune recovery is the immuno reconstitution that results from removal of leucocytes and their replacement by new leucocytes. Yet a further aspect of immune recovery may result from reduced generation of immunosuppressive cytokines (TNF-α).

Certain aspects of immune recovery appear to result from removal of infected leucocytes whilst other aspects may be fully or partly independent of leucocyte removal.

In AIDS, the CD4 leucocyte count is regarded as indicative of the status of a subject's immune system. When blood of an HIV positive person is contacted with a carrier as defined above the person's CD4 count increases, thereby demonstrating an immune improvement, and hence immune recovery. The present invention also provides use of an adsorbent carrier described above in the manufacture of an agent or adsorbent for use in apheresis for the various aspects of immune recovery described above.

The invention further provides a method for the treatment of a patient having an infection that involves infected, activated and/or defective leucocytes, which comprises bringing blood from the patient into contact with a carrier that has a higher affinity for infected, activated and/or defective leucocytes than for uninfected non-activated or non-defective leucocytes and returning the treated blood to the patient.

Particularly, the leucocytes may be activated or infected leucocytes and the cells may be brought into contact with an adsorbent carrier that has a greater affinity for activated or infected leucocytes than for normal leucocytes.

More particularly, the leucocytes may be infected leucocytes and the cells may be brought into contact with an adsorbent carrier that has a greater affinity for infected leucocytes than for normal leucocytes.

Leucocytes may be infected with a virus or with another intracellular pathogenic organism, for example, an intracellular parasitic organism. Leucocytes may be infected with a virus that stimulates the cells and brings about an activation and/or a change in the surface receptors of the cells. For example, the virus is HIV or HCV, particularly HIV. HIV has a profound effect on cells of the immune system.

As explained above, HIV infects monocytes/macrophages and CD4+ lymphocytes. Different viruses may infect different populations of leucocytes. Monocytes/macrophages may be particularly subject to infection owing to their phagocytic activity. However, different viruses may infect different populations of lymphocytes. HIV infects CD4+ lymphocytes because the virus effects entry via the CD4 receptor. Other viruses may effect entry into lymphocytes via different receptors and hence infect the population of lymphocytes that possess that particular receptor.

The leucocytes may be infected with an intracellular parasitic organism which organism brings about an activation and/or a change in the surface receptors of the cells, for example, *Mycobacterium leprae*. *Mycobacterium leprae* infects monocytes in paricular.

The invention further provides the use of an adsorbent carrier that has a greater affinity for infected, activated and/or defective leucocytes than for normal leucocytes in the manufacture of an agent for the removal of infected, activated and/or defective leucocytes from blood.

The invention further provides a method for use in flushing out (purging) infected leucocytes from resting sites in a subject, which comprises bringing blood from the subject, which blood comprises infected leucocytes into contact with an adsorbent carrier that has a greater affinity for infected leucocytes than for normal leucocytes. The treated blood may be returned to the subject to flush out infected cells from resting sites. Such flushing out of cells is commonly known in the art as "purging". The cells are especially leucocytes infected with a virus; for example, HCV or especially HIV. Such infected cells include mononuclear cells (monocytes/macrophages) and CD4+ lymphocytes. Flushing infected cells from resting sites results in the virus within the cells becoming vulnerable to drug therapy.

The invention further provides a method for use in the treatment of a disease in which infected, activated and/or defective leucocytes have a changed surface, which comprises bringing blood that comprises infected, activated and/or defective leucocytes into contact with an adsorbent carrier that has a greater affinity for infected, activated and/or defective leucocytes than for uninfected, non-activated or non-defective leucocytes. The treated blood may be returned to the patient to complete the treatment of the disease.

The types of diseases and disorders with which the present invention may be used include those in which infection of host cells, for example, with a virus or with another intracellular pathogenic, for example, parasitic organism, gives rise to an alteration of surface properties of the infected cells. For example, infection of cells of the immune system may give rise to activation of those cells, accompanied by a change in surface receptors.

The invention further provides a method for use in the treatment of a patient having a disease or disorder in which leucocytes are infected, which comprises bringing blood that comprises infected leucocytes into contact with an adsorbent carrier that has a greater affinity for infected, activated and/or defective leucocytes than for uninfected leucocytes. The treated blood may be returned to the patient to complete the treatement of the disease or disorder.

Still further, the invention provides a method for the treatment of a patient which method comprises bringing blood that comprises infected leucocytes from the patient into contact with an adsorbent carrier that has a greater affinity for infected, activated and/or defective leucocytes than for uninfected leucocytes and returning the blood to the patient.

Diseases which may be treated according to the present invention include leprosy, HCV infection and HIV infections, including ARC, AIDS and symptomless HIV infections. Still further, the invention provides the use of an adsorbent carrier in the preparation of materials for use in the above methods.

The invention further provides a method for effecting immune recovery in a patient infected with a pathogenic organism, particularly HIV, which comprises contacting blood from the patient with an adsorbent carrier that has a contact angle to water in the range between 55° and 95°. For example, the patient may be infected with HIV.

In any embodiment of the present invention the adsorbent carrier may be contacted with plasma as an alternative to whole blood. Blood may be separated into plasma and other components in an appropriate manner before treatment according to the present invention. However, it is generally simpler and cheaper to treat whole blood. In general, therefore, plasma is used only in special circumstances.

BRIEF DESCRIPTION OF DRAWINGS

The above and other features and advantages of the present invention will become apparent from the following description and the appended claims, taken in conjunction with the accompanying drawings, in which:

BEST MODE FOR CARRYING OUT THE INVENTION

Figure 1:
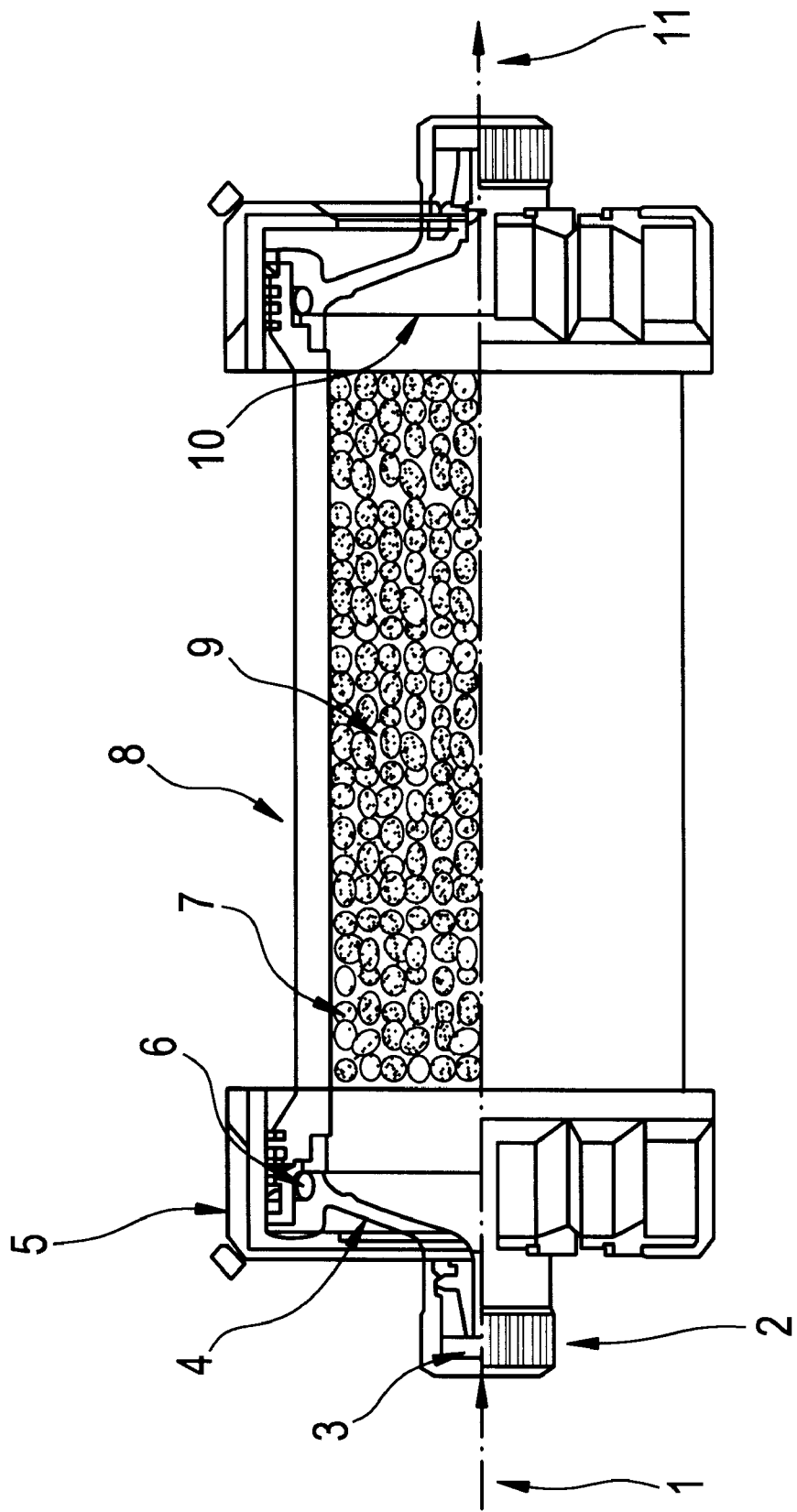
FIG. 1 outlines the structural components of a leucocyte apheresis column according to one embodiment of the invention.

The term "adsorbent carrier" is used herein to denote a material that is capable of adsorbing cells onto its surface.

The adsorbent carrier used in accordance with the invention has a higher affinity for infected, activated and/or defective leucocytes than for uninfected, non-activated or non-defective leucocytes, whilst not adversely affecting the blood brought into contact with the adsorbent.

The efficiency with which a particular cell type is adsorbed by a particular adsorbent carrier is calculated as:

Trapping efficiency (%)=No. of cells adsorbed/No. of cells exposed to the adsorbent carrier×100

Differential leucocyte counts (counts of a particular leucocyte type) are determined by a standard laboratory differential leucocyte counter, for example THMS H-1 (Technicon). The number of cells of a particular leucocyte type trapped by the carrier in the column is calculated by subtracting the appropriate leucocyte count in the blood at the column outlet from the corresponding leucocyte count in the blood at the column inlet. The number of cells exposed to the carrier is calculated from the flow rate (ml per minute), flow time (apheresis time) and the appropriate leucocyte count at the inflow.

An example of an adsorbent carrier that may be used according to the present invention is an adsorbent carrier the contact angle to water of which falls within a range of from 55° to 95°.

The term "contact angles" is used herein to denote an angle formed by a free surface of a stationary liquid and a solid surface at a point where the free surface is in contact with the solid surface. The angle located inside the liquid is employed. Contact angles of principal adsorbent carriers to water are summarised as shown below in Table 1.

TABLE 1

| Material | Contact angle to water (°) |
| --- | --- |
| Cellulose acetate | 60 |
| Polystyrene | 91 |
| Nylon | 70 |
| Polytetrafluoroethylene (TEFLON) (Reference compound.) | 108 |
| Polytrifluoroethylene | 92 |
| Polyethylene terephthalate | 81 |
| Polyethylene | 94 |
| Polyvinyl chloride | 87 |
| Polyvinyl alcohol (Reference compound) | 36 |
| Acrylic resin (Reference compound) | 54 |
| Glass (Reference compound) | 8 |
| Ethylcellulose | 64 |

An adsorbent carrier with a contact angle within the range of from 55° to 95°, for example those mentioned in Table 1, is suitable for adsorption of activated, infected or defective leucocytes including mononuclear cells (monocytes/ macrophages), neutrophils and $CD4^+$ lymphocytes, whereby effective removal of activated leucocytes including mononuclear cells (monocytes/ macrophages), neutrophils and $CD4^+$ lymphocytes from the liquid may be achieved. Moreover, adsorption of other blood cell components, plasma components and serum components may be minimised. Two or more adsorbent carriers may be used in combination.

Polystyrene, cellulose acetate, nylon, for example, 6-nylon or 11-nylon, polytrifluoro-ethylene and polyethylene terephthalate are particularly suitable as adsorbent carriers according to the present invention. Cellulose acetate is a particularly preferred adsorbent carrier.

No particular limitation is imposed on the choice of shape and size of the adsorbent carrier. It is, however, preferable that the adsorbent carrier has a size distinguishable from blood cells and a shape having a large contact area with the blood to be brought into contact therewith, to permit efficient contact. For example, the adsorbent carrier may take the form of beads having a diameter of about 0.1–10 mm. Suitably the beads may have a diameter in the range of from 0.2 to 5.0 mm. Preferably, the beads may have a diameter in the range of from 0.5 to 4.0 mm. More preferably, the beads may have a diameter in the range of from 1.0 to 3.0 mm, for example 2.0 mm.

The efficiency of cell removal by the adsorbent carrier may be enhanced when the adsorbent carrier has a roughened surface. This is particularly the case when the adsorbent carrier has on its surface roughness having a centre line average height Ra, being defined under Japanese and Industrial Standard B0601-1982, of 0.2 µm to 10 µm and a mean spacing Sm of unevenness within the range from 5 µm to 200 µm. The effectiveness of an apheresis adsorbent carrier with such surface characteristics has been described in U.S. Pat. No. 5,593,586 and a method of making such an adsorbent carrier has been described in U.S. Pat. No. 5,525,279.

As indicated above, cellulose acetate is a particularly preferred material for the adsorbent carrier. Preferably, a cellulose acetate adsorbent carrier may take the form of beads, for example having a diameter of in the range from about 0.1–10 mm, for example, from 0.2 to 5.0 mm, for example from 0.5 to 4.0 mm, for example from 1.0 to 3.0 mm, for example 2.0 mm.

The effectiveness of cell removal by a cellulose acetate adsorbent carrier is generally enhanced when the adsorbent carrier has a roughened surface, particularly as described above.

A leucocyte removal device for use in a method of the present invention comprises a means for bringing blood that comprises infected, activated and/or defective leucocytes into contact with the adsorbent carrier such that the blood is treated with the carrier and then recovered. The blood of the patient who is being treated is preferably peripheral blood. The device may also include a means for transporting blood back to the patient. One or both of the transferring means may include a pumping means. One or both of the transferring means may include a means for measuring the rate of flow and/or the pressure of the blood within the transferring means. Optionally, a means for adding pharmaceutical agents to the blood may be present on one or both of the transferring means.

A leucocyte apheresis column for use in a method of the invention is a column filled with the adsorbent carrier, particularly an adsorbent carrier in the form of beads, bathed in physiological liquid, particularly sterile, physiological saline. Blood is supplied to the column via a blood inlet, and blood leaves the column via a blood outlet. Optionally, the blood inlet is connected to a suitable blood vessel in a patient, such as a vein in an arm or a hand, generally via a transporting means, for example a tube. Similarly, the blood outlet may be connected to a further suitable blood vessel in a patient, such as a vein in an arm or a hand.

The precise protocol for use of a device according to the present invention and the method of its use will be a matter of clinical judgement in each individual case.

The flow rate of blood through a leucocyte apheresis device according to the present invention may be within the range of from 5 to 200 ml/min. Preferably it is from 20 to 50 ml/min. At high flow rates haemolysis owing to shearing may be disadvantageous. The duration of apheresis may be in the range of from 10 minutes to 10 hours. The exact duration will be a matter of clinical judgement in each individual case. The frequency of treatment will also be a matter of clinical judgement in each individual case. Typically, a regime of one apheresis of one hour's duration once per week at, for example, 30 ml/min flow rate may be used.

The removal of infected, activated and/or defective leucocytes according to the present invention may be part of the treatment of a disease or disorder. The disease is, for example, HCV infection, leprosy or HIV infection, for example, AIDS. As indicated above, the preferred adsorbent carrier is cellulose acetate, for example, in the form of beads. An example of a treatment protocol is given above.

In a further embodiment of the invention immune recovery in a patient infected with a pathogenic organism is effected by contacting blood from the patient with a carrier having a contact angle to water within the range of from 55° to 95° and returning the blood to the patient. The absorbent carrier may be as described above, and is preferably cellulose acetate, especially in one of the preferred forms described above.

When the method of the invention is carried out, the above described effects relating to leucocyte removal and the immune recovery both occur.

Immune recovery denotes an improvement in any one or more aspects of the immune system. One aspect of immune recovery is an immunological improvement. HIV has a particularly profound effect on a subject's immune system.

Another aspect of immune recovery is the immuno reconstitution that results from removal of leucocytes and their replacement by new leucocytes. Yet a further aspect of immune recovery may result from reduced generation of immunosuppressive cytokines (TNF-α).

Certain aspects of immune recovery appear to result from removal of infected leucocytes whilst other aspects may be fully or partly independent of leucocyte removal.

In AIDS, the CD4 leucocyte count is regarded as indicative of the status of a subject's immune system. When blood of an HIV positive person is contacted with a carrier as defined above the person's CD4 count increases, thereby demonstrating an immune improvement, and hence immune recovery. The present invention also provides use of an adsorbent carrier described above in the manufacture of an agent or adsorbent for use in apheresis for the various aspects of immune recovery described above.

The present invention has the following effects in the case of treatment of AIDS particularly when the blood is contacted with cellulose acetate:

a) Infected leucocytes including monocytes/macrophages are removed from the blood and as a consequence of this action production of leucocytes is increased and latently infected leucocytes are mobilized from resting sites in the patient.

b) As a result of the action described in (a), a decrease in the plasma HIV-1 RNA and a decrease in total HIV-1 DNA (including integrated HIV-1 pro viral DNA load in latently infected cells) is achieved.

c) Removal of infected leucocytes and increased production and mobilization of leucocytes results in a decrease in the number of resting memory T-cells (CD4$^+$/CD45$^+$RO), the latently infected CD4$^+$ lymphocytes which can be reservoirs of HIV, and an increase the number of naive T-cells (CD4$^+$/CD45$^+$RA).

d) The actions of the present treatment approach described in (a), (b) and (c) above can flush out ("purge") the HIV-infected leucocytes from resting sites with the result that the integrated HIV-1 proviral DNA load in the latently infected CD4$^+$ lymphocyte reservoir becomes vulnerable to drug therapy.

e) In patients with HIV, peripheral blood leucocytes including monocytes/macrophages and neutrophils are known to produce increased amounts of proinflammatory or immunosuppressive cytokines, TNF-α, IL-1β, IL-6, IL-10 (see above). Production of these cytokines is suppressed by the present invention.

f) As a result of actions in (a) and (e) above, T-cell activity increases, for example, $CD4^+/CD25^+$ increases. $CD4^+/CD25^+$ represents T-cell activity; these are activated T-cells (CD25 is the receptor for IL-2). The increase in $CD4^+/CD25^+$ is very important for HIV patients because:
   1) they produce IL-2,
   2) by being activated, they activate proviral DNA and make it vulnerable to HAART (drugs).

g) By analogy to but independently of (f), the number of $CD4^+$ T-cells and $CD8^+$ T-cells may be increased by a method of the present invention. This demonstrates immune recovery.

h) Patients with HIV infection are known to have increased levels of immune complexes bound to HIV antigens such as gp120; immune complex-gp120 is believed to induce apoptosis of $CD4^+$ cells. Based on the evidence in the literature (18), we believe method of the present invention can remove IgG-containing immune complexes.

Changes in TNFα and IL-12 production as well as CD4 counts were maintained througout the follow-up period (7 weeks after cessation of the G-1 apheresis).

The removal of infected cells has analogous effects in the treatment of Hepatitis C and leprosy.

Many drug therapies of HIV, HCV and leprosy are known to have side-effects, often severe side-effects which reduce the quality of life of the patient. Apheresis has minimal side effects as no substances are administered to the patient. The disease state may therefore be improved with very little discomfort or health risk to the patient. Patients who have received apheresis treatment involving removal of leucocytes according to the present invention report no unpleasant effects from the treatment.

A leucocyte apheresis apparatus according to one embodiment of the invention will now be described by way of example only with reference to FIG. 1 and FIG. 2 of the accompanying drawings.

Figure 2:
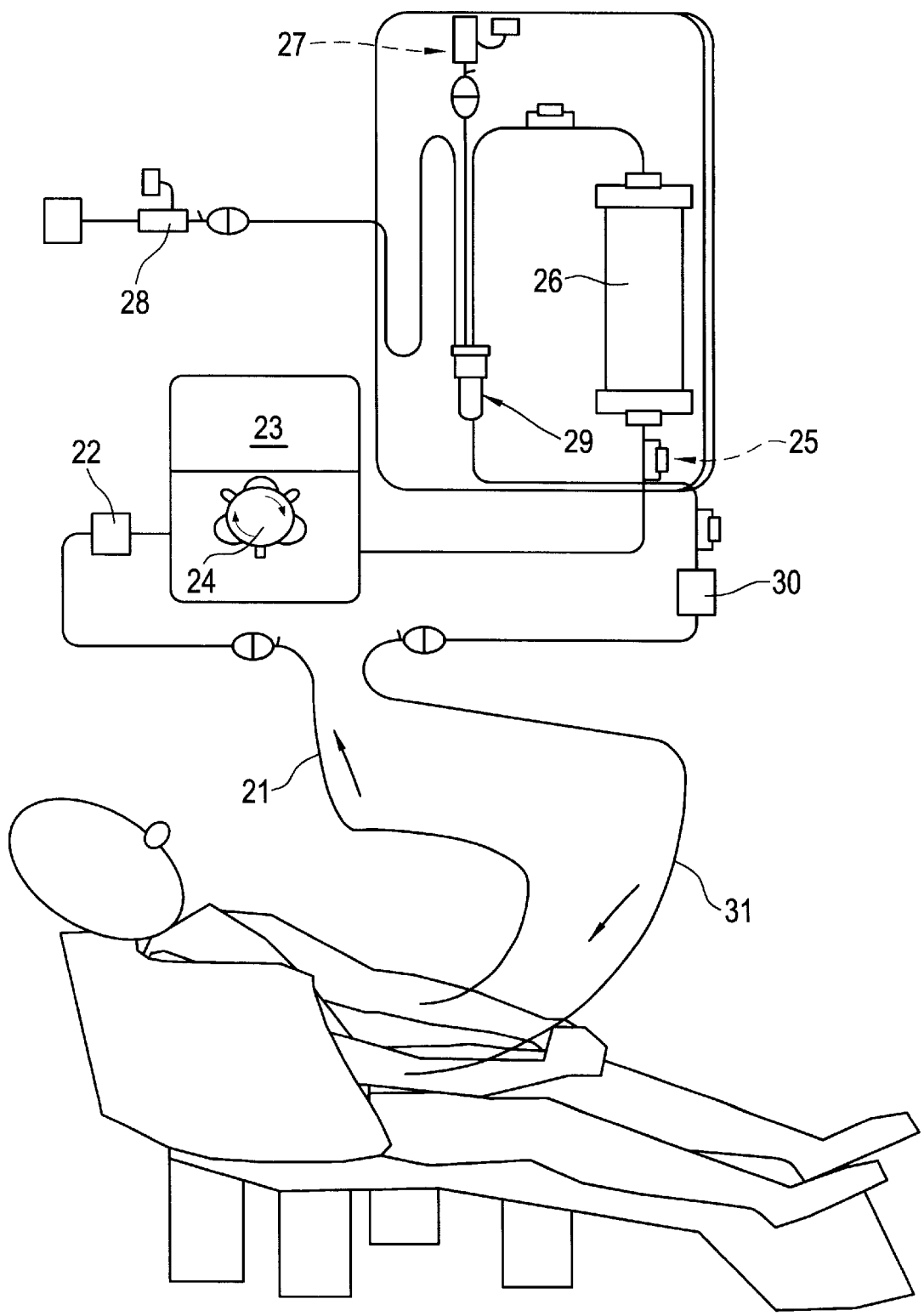
FIG. 2 illustrates the components of a leucocyte apheresis device according to one embodiment of the invention.

FIG. 1 outlines the structural components of a leucocyte apheresis column according to one embodiment of the invention;

FIG. 2 illustrates the components of a leucocyte apheresis device according to one embodiment of the invention.

Leucocyte Apheresis Column

An apheresis column is an adsorbent-type extracorporeal leucocyte apheresis device. The device column is filled with cellulose acetate beads (adsorbent carriers) of 2 mm diameter, bathed in sterile physiological saline. The finished assembly is then sterilized and thoroughly leak tested by standard procedures. Blood inlet and outlet are via suitable veins in the left and the right hands. The system has been developed for selective adsorption of activated or infected leucocytes including monocytes/macrophages and neutrophils by a process known as leucocyte apheresis. Normal, non-activated non-infected lymphocytes do not adhere to the column adsorbent carriers. Additionally, research results published in the literature suggest that IgG immune complexes bind to cellulose acetate surface (18), which may provide an additional advantage.

Components of the G-1 Column Leucocyte Apheresis Device

The structure of the G-1 column (Adacolumn) a device formed according to the present invention is presented in FIG. 1 and the materials of its components are described in Table 1. An outline of the G-1 column leucocyte apheresis device is presented in FIG. 2.

As shown in FIG. 1, the G-1 column comprises a polycarbonate column (Adacolumn (8)) which is filled with cellulose acetate beads (adsorbent carriers (7)) bathed in physiological saline (9). The column contents are sealed by inner cap (4), outer cap (5) and O-ring (6). The blood supply line is secured onto the column by a nozzle cap (2) and packing (3) at the blood inlet (1) The adsorbent carriers have a diameter of 2 mm with a total weight of 220 g. The polycarbonate column is 206 mm in length and 60 mm in diameter and has a capacity of 335 ml. The total volume of the physiological saline is 130 ml (equal to the column void volume).

The constituents of the G-1 column (Adacolumn) are shown below in Table 2.

TABLE 2

Constituents of the G-1 Column (Adacolumn)

| Name | Raw Material |
| --- | --- |
| Adsorbent carrier* | Cellulose acetate |
| Main body* | Polycarbonate |
| Outer cap* | Polypropylene |
| Inner cap* | Polypropylene |
| O-ring* | Silicone rubber |
| Perforated stopper* | Polyethylene terephthalate |
| Packing | Silicone rubber |
| Nozzle cap | Polypropylene |
| Filling solution | Isotonic physiological saline |
| Circuit lines | PVC (polyvinylchloride, plasticised) Nylon/polypropylene laminate film, partially gas-permeable |
| Packaging film | wood-free paper or nonwoven fabric (Nylon/C. P. P. film) |

*Indicates that the component comes into direct contact with the blood.

As shown in FIG. 2, the G-1 leucocyte apheresis device comprises a polycarbonate column (Adacolumn (26)), blood circuit lines and an Adamonitor (23) together with a pump (24). The blood outflow from an antecubital vein of the patient (21) passes through a bubble detector (22) to a pump (24) and an Adamonitor (23). The blood then passes an anticoagulant administration port (25) before entering an adacolumn (26). Following outflow from the column, the blood enters drip chamber (29) to which are attached a drip chamber air outlet port (27) and venous pressure gauge (28). After passing a bubble detector (30), the blood flows back into the patient via an antecubital vein (31).

The following non-limiting Examples illustrate the invention.

EXAMPLES

Examples 1 to 10

HIV-1-infected patients who were receiving HAART, but had developed resistance or were partial responders to HAART were selected for apheresis therapy according to the selection criteria given below. The results of apheresis therapy are presented Examples 1 to 9 below and in FIGS. 3 to 14.

Figure 3:
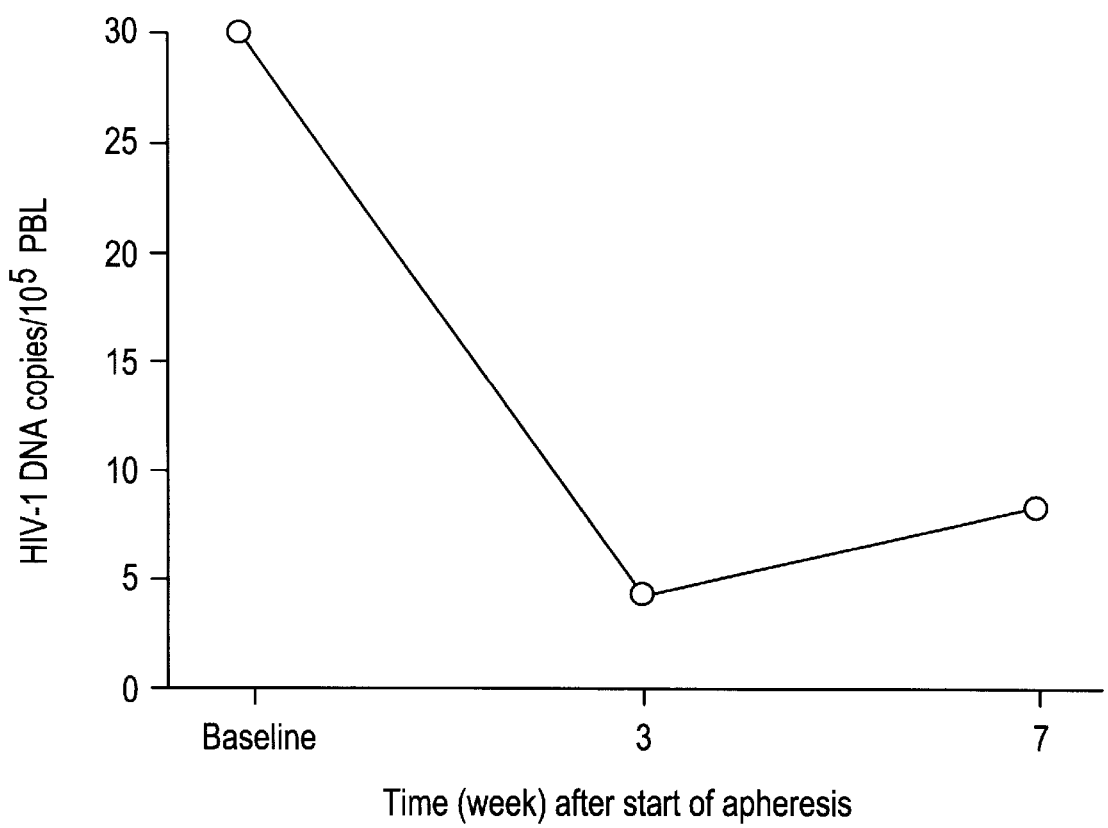
FIG. 3 to FIG. 14 show biological changes in patients undergoing treatment using a method according to one embodiment of the invention.

FIG. 3. A graph showing the change in the number of copies of HIV-1 DNA per $10^5$ peripheral blood lymphocytes (PBL) with time (in weeks) during the course of apheresis treatment of a patient with low HIV-1 DNA count before apheresis treatment.

Figure 4:
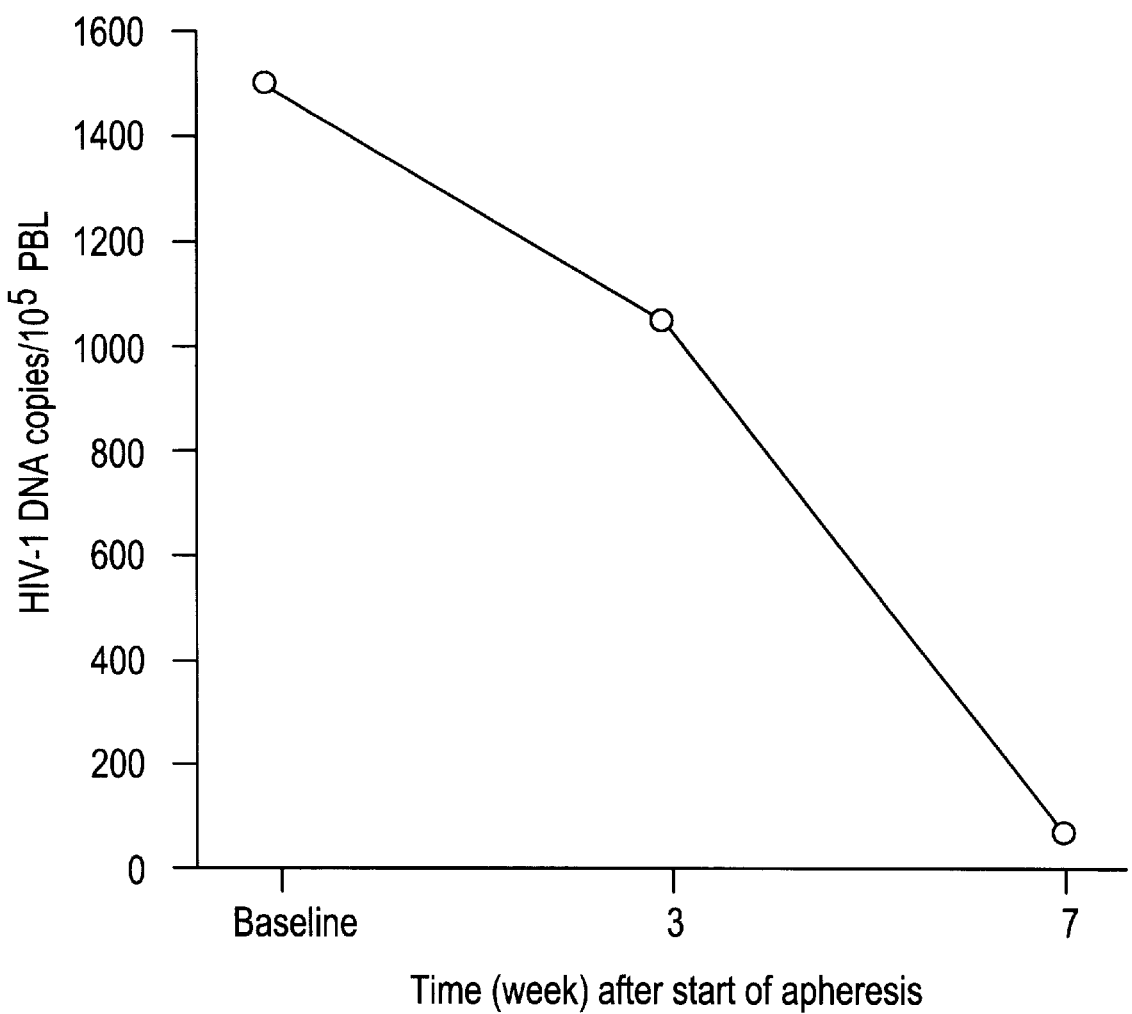

FIG. 4. A graph showing the change in the number of copies of HIV-1 DNA per $10^5$ peripheral blood lymphocytes (PBL) with time (in weeks) during the course of apheresis treatment of a patient with high HIV-1 DNA count before apheresis treatment.

Figure 5:
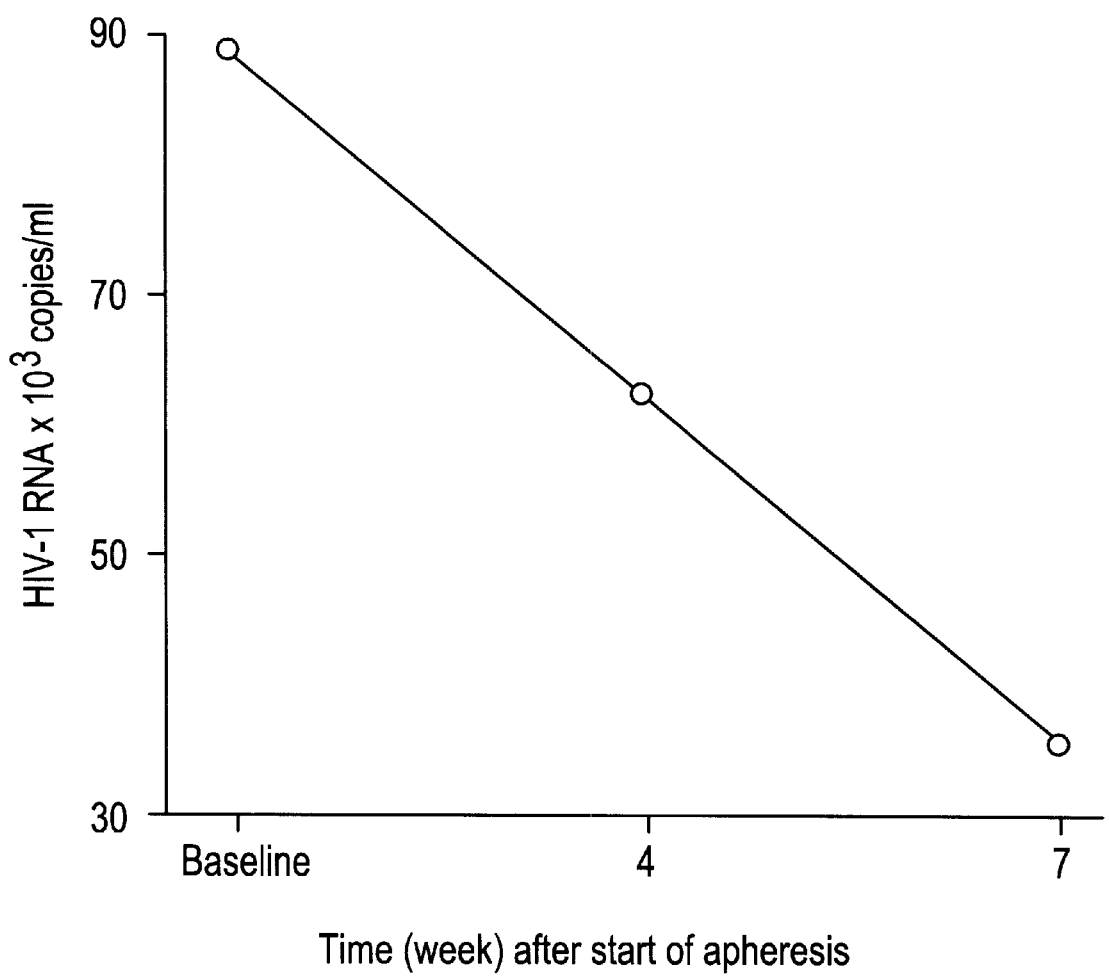

FIG. 5. A graph showing the change in the number of copies of HIV-1 RNA (×10³) per ml blood with time during the course of apheresis treatment of an HIV-infected patient.

Figure 6:
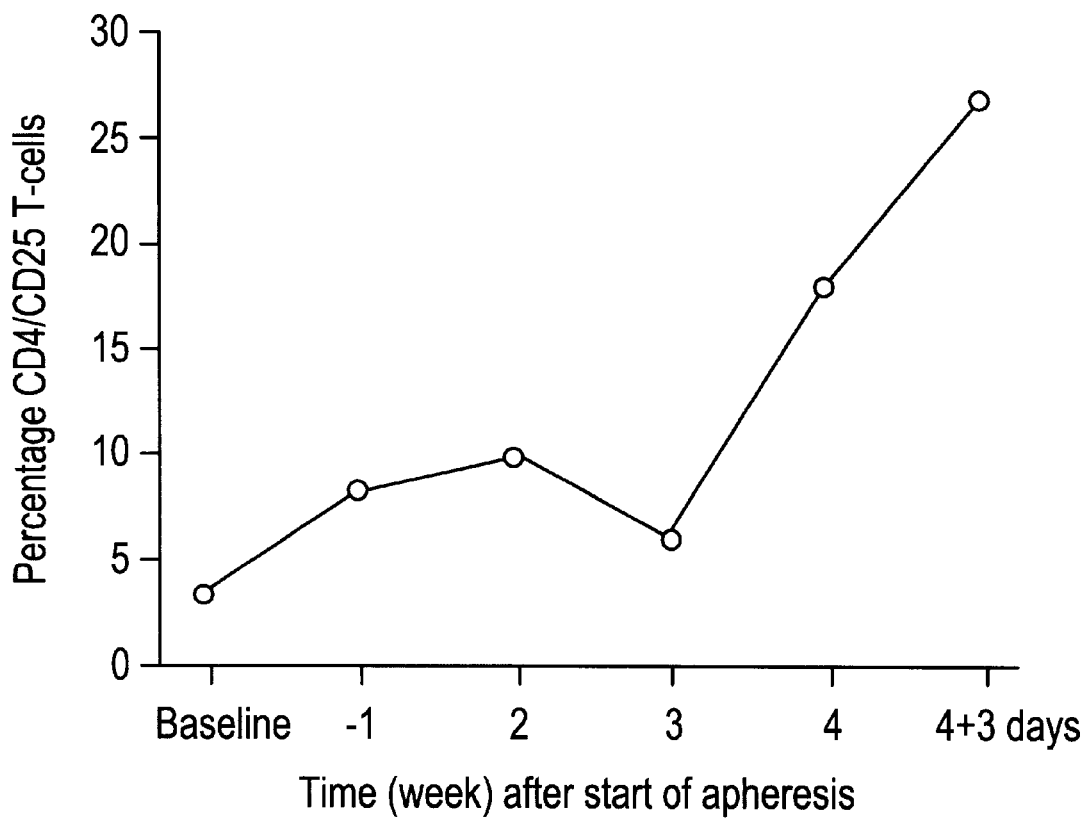

FIG. 6. A graph showing the change in the percentage of CD4+/CD25+ T-Cells with time (in weeks) during the course of apheresis treatment of an HIV-infected patient.

Figure 7:
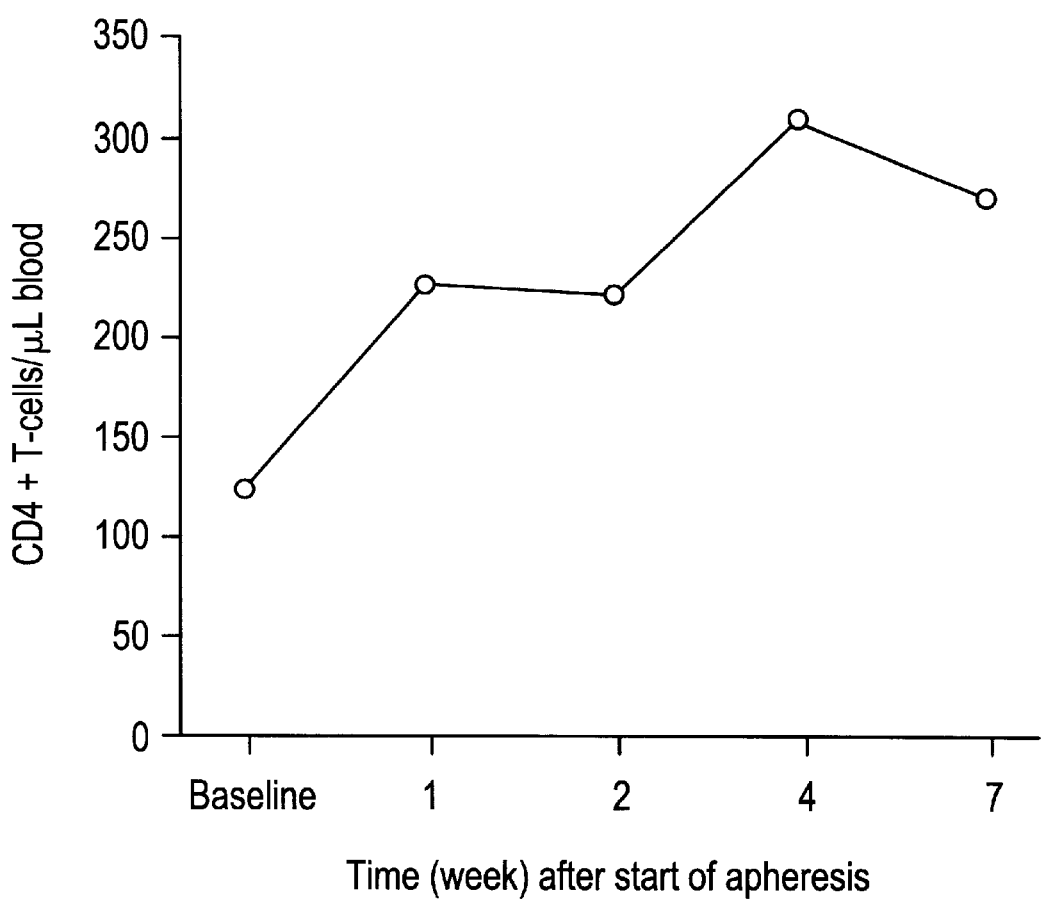

FIG. 7. A graph showing the change in the number of CD4+ T-cells per μl blood with time (in weeks) during the course of apheresis treatment of an HIV-infected patient.

Figure 8:
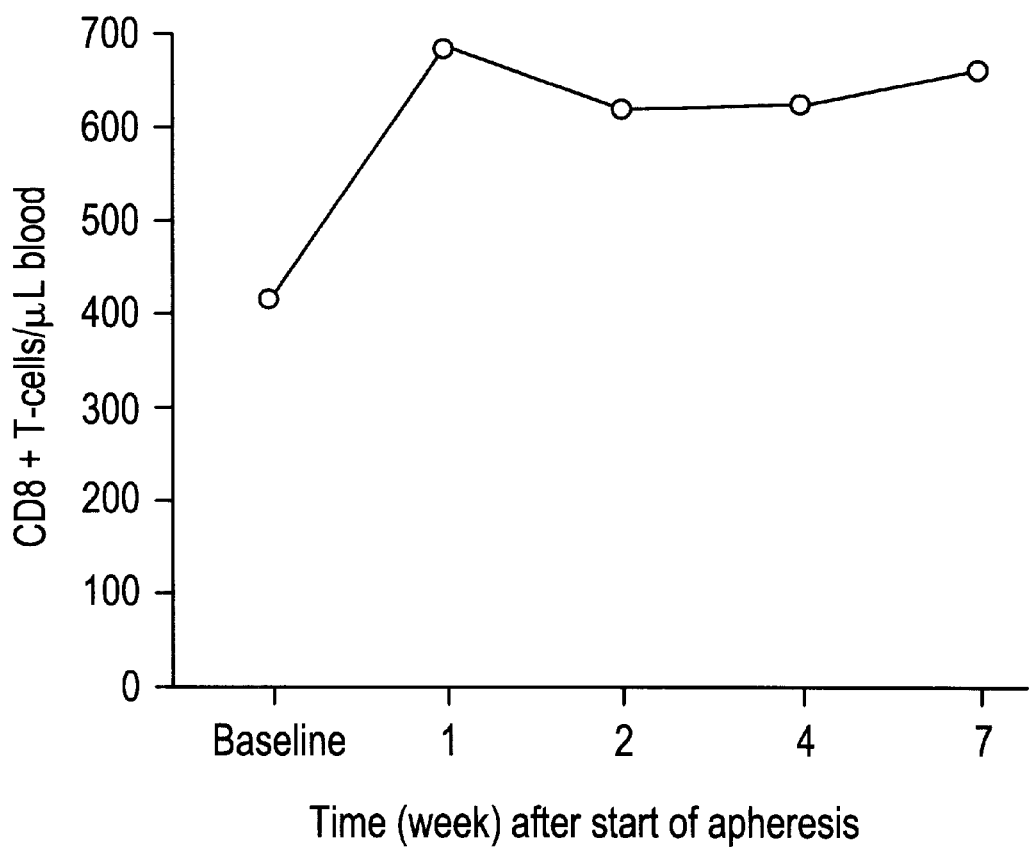

FIG. 8. A graph showing the change in the number of CD8+ T-cells per μl blood with time (in weeks) during the course of apheresis treatment of an HIV-infected patient.

Figure 9:
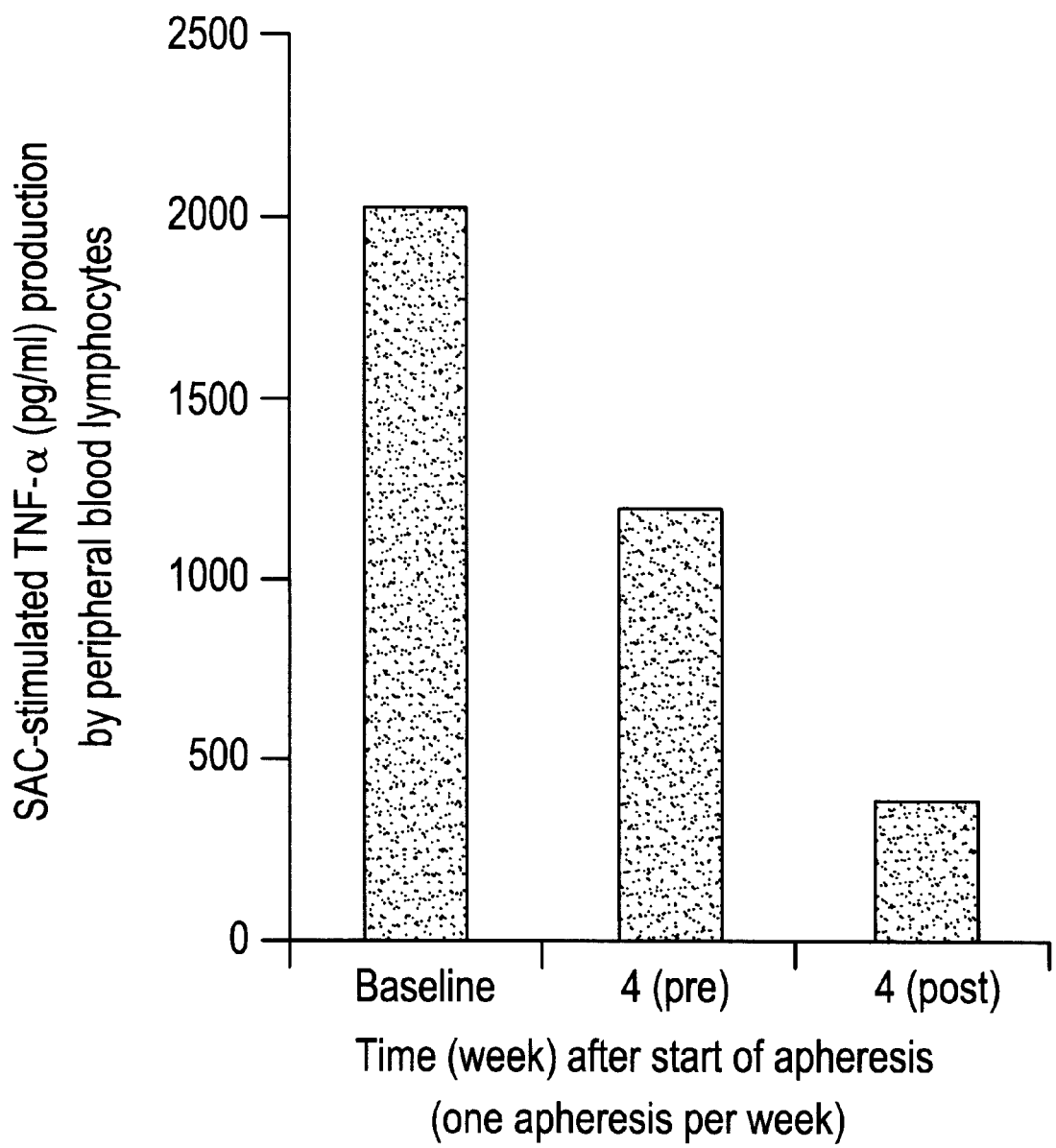

FIG. 9. A graph showing the change in SAC-stimulated TNF-α production by peripheral blood mononuclear cells (in pg/ml) with time (in weeks) during the course of apheresis treatment of an HIV-infected patient. SAC is the superantigen of staphilococcus aureus.

Figure 10:
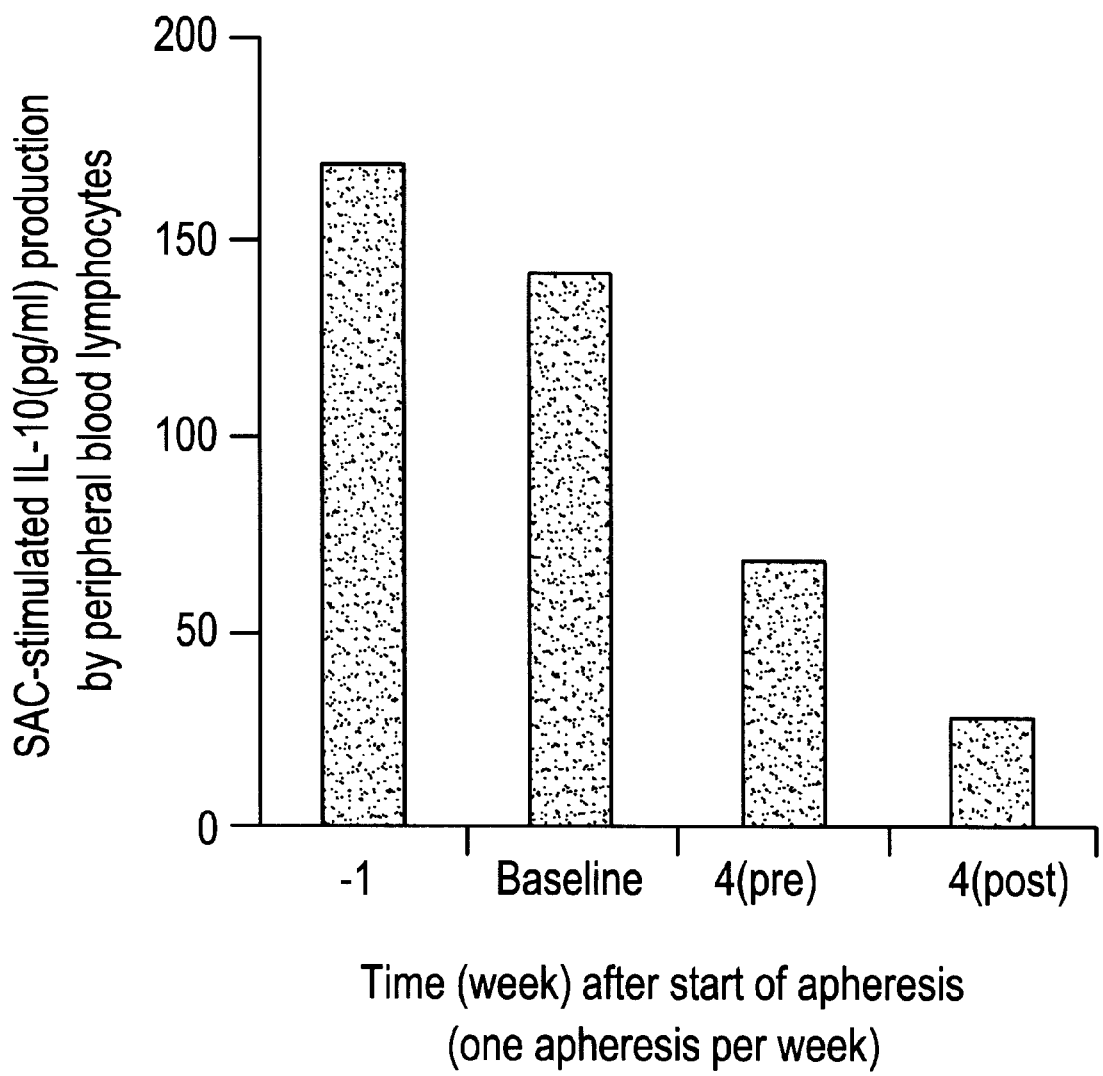

FIG. 10. A graph showing the change in SAC-stimulated IL-10 (interleukin 10 in pg/ml) with time (in weeks) production by peripheral blood mononuclear cells during the course of apheresis treatment of an HIV-infected patient.

Figure 11:
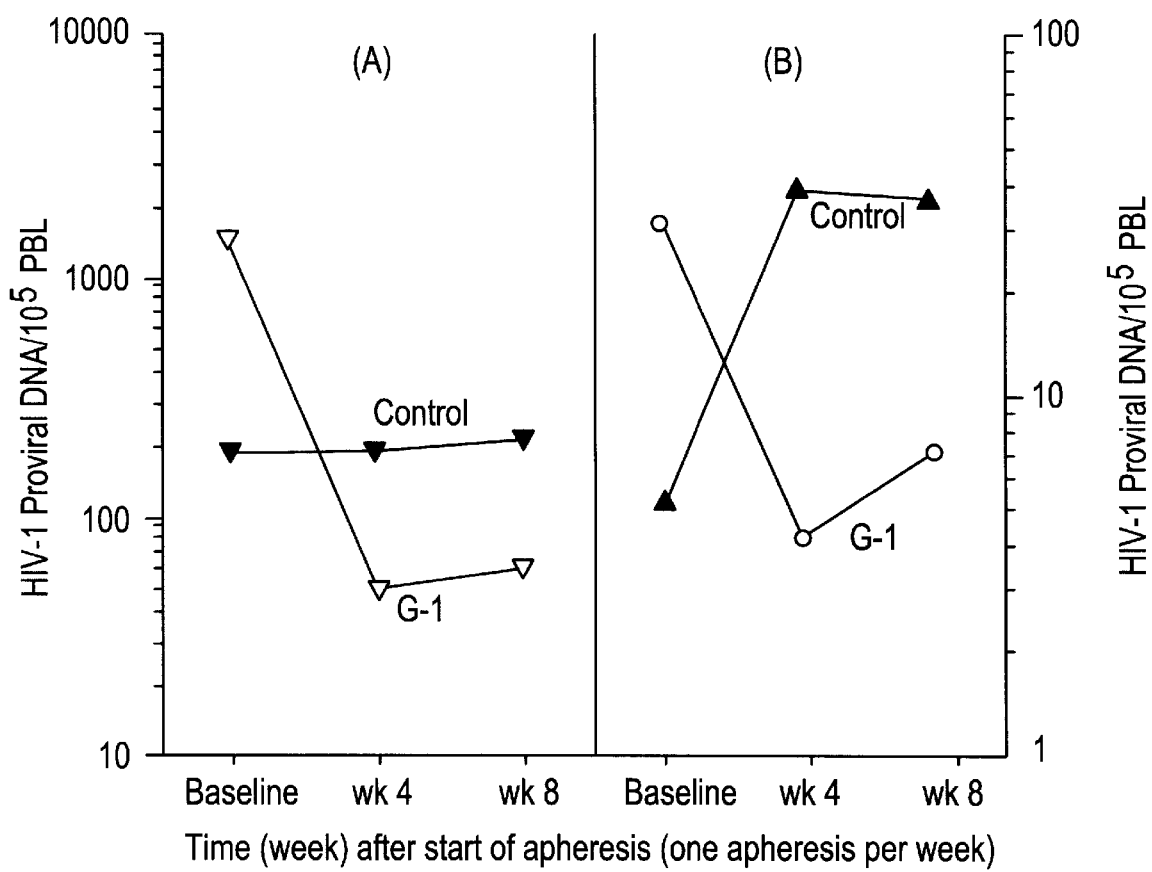

FIG. 11. A graph showing the change in HIV-1 proviral DNA levels per $10^5$ peripheral blood lymphocytes (PBL) in patients A and B with time (in weeks) during the course of apheresis treatment.

Figure 12:
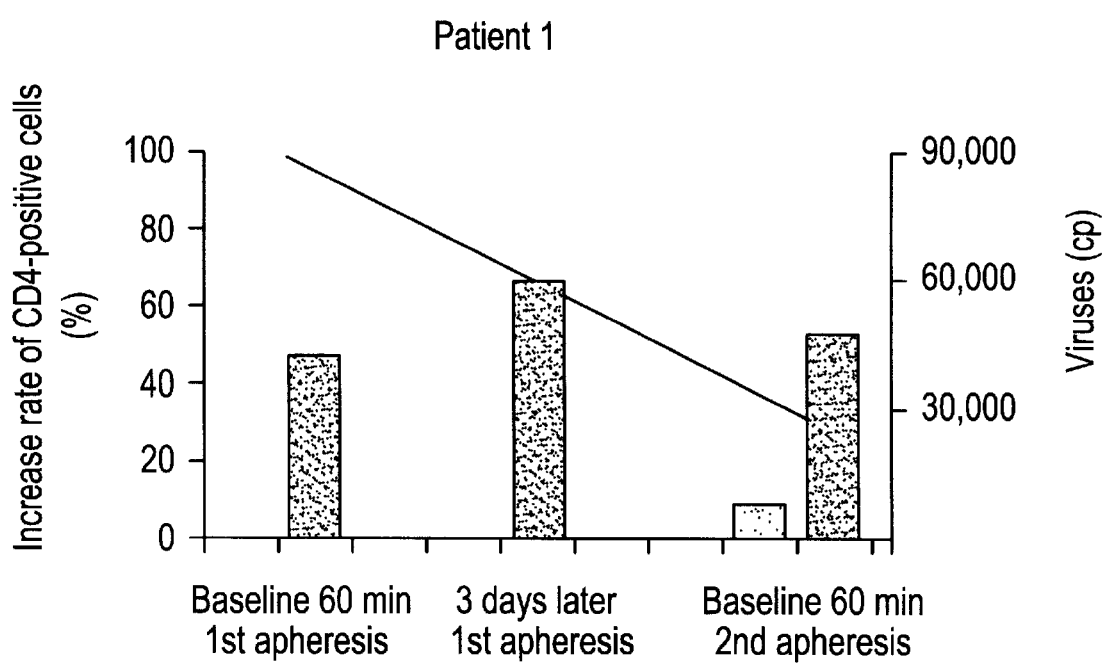

FIG. 12. A graph showing the change in the level of CD4-positive cells (% increase) and the change in viral load (copies per ml) with time in patient 1 undergoing apheresis treatment.

Figure 13:
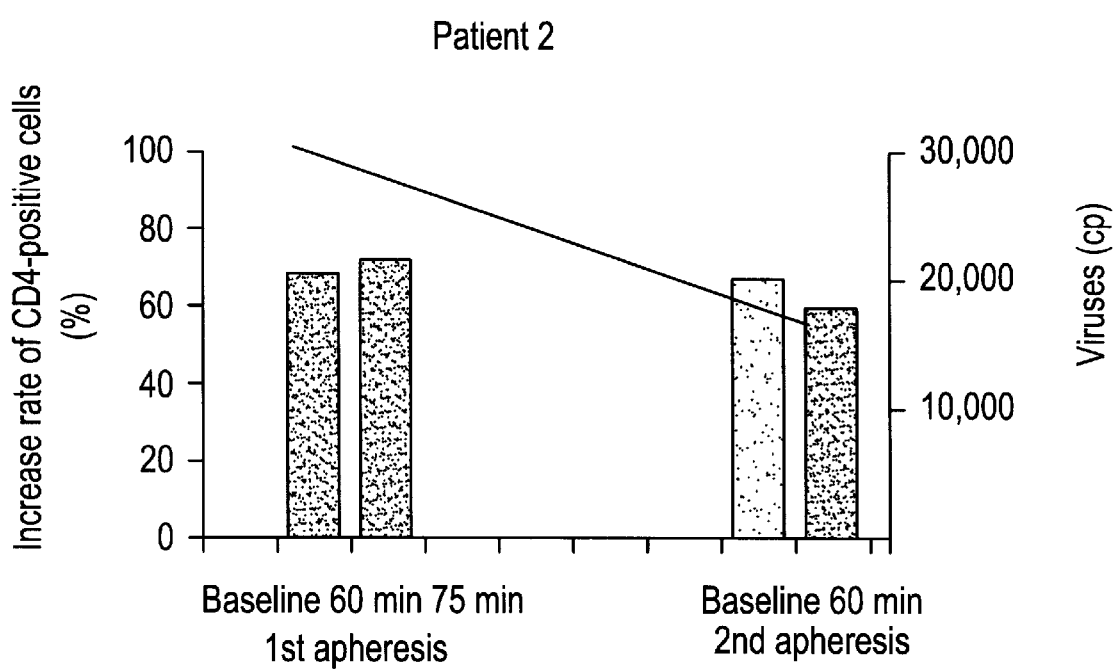

FIG. 13. A graph showing the change in the level of CD4-positive cells (% increase) and the change in viral load (copies per ml) with time in patient 2 undergoing apheresis treatment.

Figure 14:
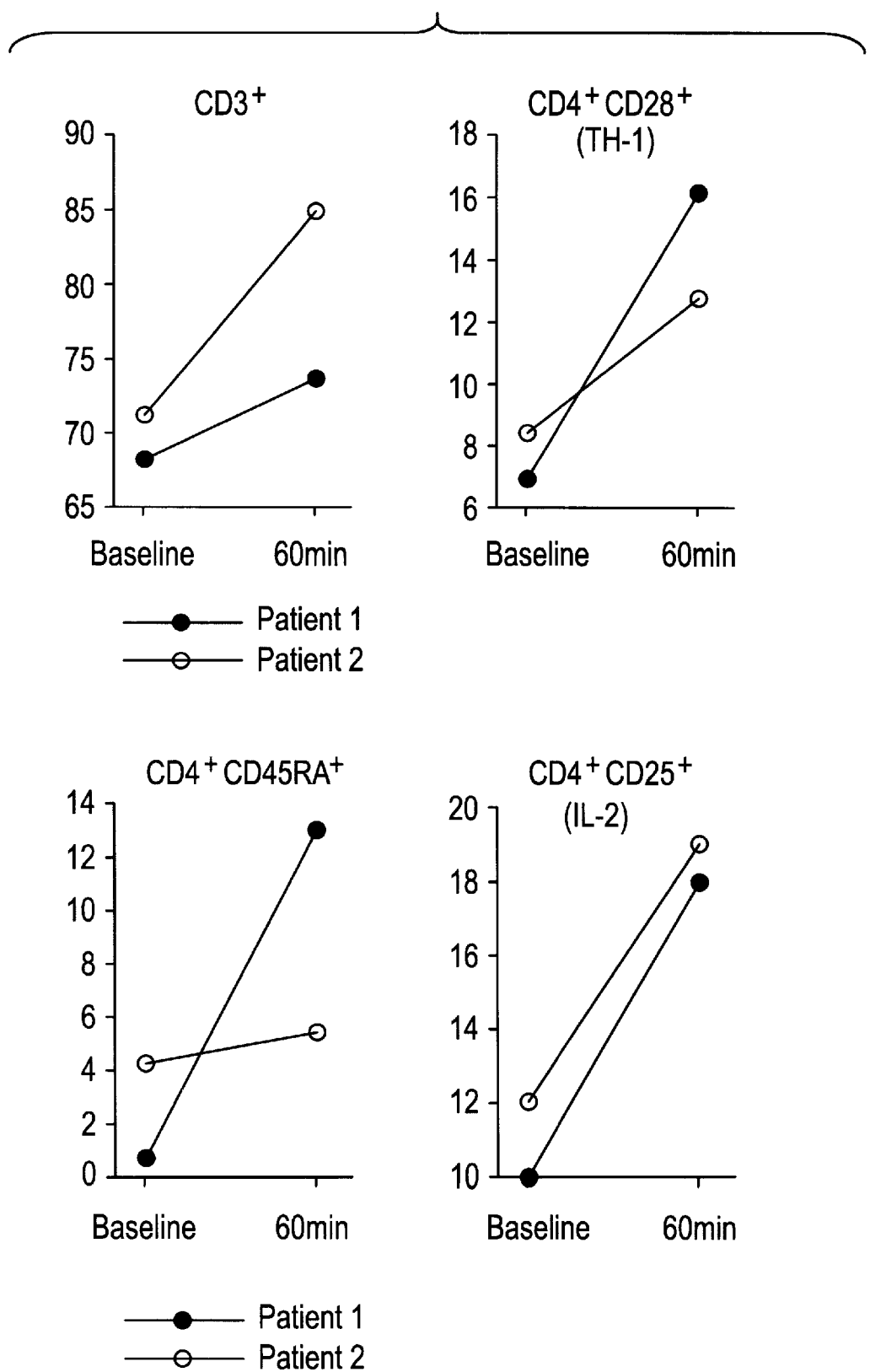

FIG. 14. Graphs showing the changes in levels of CD3+ cells (as a percentage of lymphocytes), CD4+CD28+ (TH-1) cells (the percentage of CD28+ cells based on CD4+ cells), CD5+CD-45RA+ (the percentage of CD45RA+ cells based on the CD4+ cells) cells and CD4+CD25+ (IL-2) (the percentage of CD25+ cells based on CD4+ cells) cells before and after treatment in patients 1 and 2 undergoing apheresis treatment.

Apheresis Time and Study Duration

Patients under HAART received apheresis treatment using the G-1 column described above. Each patient received one apheresis per week over an 8 week period. Each apheresis is of 60 minutes duration at a flow rate of 30 ml/minute.

Selection Criteria a) Documented HIV infection, b) Male or non-pregnant, non-lactating females over 18 years of age, c) Ability and willingness to give written informed consent, conforming to Italian guidelines, the declaration of Helsinki and international and institutional guidelines, and comply with the investigational nature of the study, d) On stable HAART drug therapy for at least 4 months Example 1

Treatment of an HIV-infected Patient Who Had a Low HIV DNA Count at Baseline

Baseline was the level of HIV-1 DNA before apheresis treatment was commenced. Immediately after baseline blood sampling, the patient received apheresis; one apheresis per week, at a flow rate of 30ml per minute, duration of each apheresis was 60 minutes. The fall in HIV-1 DNA following apheresis with the G-1 column is shown in FIG. 3. HIV-1 DNA was quantified using a standard quantitative polymerase chain reaction assay (Amplicor HIV Monitor™, Roche, Basel, Switzerland) on peripheral blood mononuclear cells. The results indicate that apheresis with the G-1 column can flush out the HIV-infected resting cells. No drug is known that can produce such a rapid fall in HIV-DNA load.

Example 2

Treatment of an HIV-infected Patient Who Had a High HIV DNA Count at Baseline

Immediately after baseline blood sampling, the patient received apheresis; one apheresis per week, at a flow rate of 30 ml per minute, duration of each apheresis was 60 minutes. The fall in HIV-1 DNA by apheresis with the G-1 column is shown in FIG. 4. Again (as in the case of Example 1), the results indicate that apheresis with the G-1 column can flush out the HIV-infected resting cells. No drug is known that can produce such a rapid fall in HIV-DNA load.

Example 3

The Fall in HIV-1 RNA During Treatment of an HIV-infected Patient

Immediately after baseline blood sampling, the patient received apheresis; one apheresis per week, at a flow rate of 30 ml per minute, duration of each apheresis was 60 minutes. The fall in HIV-1 RNA following apheresis with the G-1 column is shown in FIG. 5. HIV-1 RNA was quantified using a standard quantitative reverse transcriptase-polymerase chain reaction competition assay. No drug or drug therapy is known to produce such a rapid sharp decline in HIV RNA.

Example 4

The Rise in Percentage CD4+/CD25+ T-cells During Treatment of an HIV-infected Patient Immediately after baseline blood sampling, the patient received apheresis; one apheresis per week, at a flow rate of 30 ml per minute, duration of each apheresis was 60 minutes. The rise in percentage CD4+/CD25+ T-cells following apheresis with the G-1 column is shown in FIG. 6. The number of CD4+/CD25+ lymphocytes was measured using an Epics XL flow cytometer (Coulter Electronics, Inc.) using 100 μl of EDTA peripheral blood incubated for 30 minutes at 4° C. with phycoerytrin fluorochrome-labelled anti CD25 monoclonal antibody.

CD4+/CD25+ represents T-cell activity; CD4+/CD25+ T-cells are activated T-cells. CD25 is the a-subunit of the IL-2 receptor which is required for high affinity binding of IL-2. It is expressed by activated but not by resting T-cells. The increase in CD4+/CD25+ is very important for HIV patients because 1) they produce IL-2, 2) activated T-cells activate proviral DNA and make it susceptible to HAART (drugs). This facilitates the flushing out of latently infected lymphocytes (infected resting cells).

Example 5

The Rise in CD4+ T-cells Following Treatment of an HIV-infected Patient

Immediately after baseline blood sampling, the patient received apheresis; one apheresis per week, at a flow rate of 30 ml per minute, duration of each apheresis was 60 minutes. The rise in CD4+ T-cells following apheresis with the G-1 column is shown in FIG. 7. The number of CD4+ lymphocytes was measured using an Epics XL flow cytometer (Coulter Electronics, Inc.) using 100 μl of EDTA peripheral blood incubated for 30 minutes at 4° C. with phycoerytrin-Texas-Red fluorochrome-labelled anti CD4 monoclonal antibody.

CD4+ T-cell count is a key marker of HIV-disease symptoms; an increase in CD4+ T-cell count is often regarded as a marker of HIV decline and patient improvement.

Example 6

The Rise in CD8+ T-cells Following Treatment of an HIV-infected Patient

Immediately after baseline blood sampling, the patient received apheresis; one apheresis per week, at a flow rate of 30 ml per minute, duration of each apheresis was 60 minutes. The rise in CD8+ T-cells following apheresis with the G-1 column is shown in FIG. 8. The number of CD8+ lymphocytes was measured using an Epics XL flow cytometer (Coulter Electronics, Inc.) using 100 μl of EDTA peripheral blood incubated for 30 minutes at 4° C. with fluorescin-isothiocyanate fluorochrome-labelled anti CD8 monoclonal antibody.

CD8+ T-cells are caused to proliferate by raised levels of IL-2 (acting via the IL-2 receptor as described in relation to Example 4 above).

Example 7

The Decline in TNF-α Production by Peripheral Blood Mononuclear Cells Following Treatment of an HIV-infected Patient Immediately after baseline blood sampling, the patient received apheresis; one apheresis per week, at a flow rate of 30 ml per minute, duration of each apheresis was 60 minutes. The sharp decline in TNF-α production by peripheral blood mononuclear cells is shown in FIG. 9. The production of TNF-α by peripheral blood mononuclear cells(PBMC) was measured by culturing $3\times10^6$ PBMC per well in 24-well LINBRO plates (Flow laboratories, Inc. McLean, Va.) at 37° C. in a moist, 7% $CO_2$ atmosphere. The PBMC were then unstimulated or stimulated with LPS (SIGMA Diagnostics St. Louis, Mo.) at a concentration of 1 μg/ml. The supernatant was harvested after 48 hours of culture and cytokine production was then evaluated with a commercially available ELISA assay (Genzyme, Cambridge, Mass.).

TNF-α is a major pathological factor in HIV-infection disease. No drug is known that can produce such a rapid reduction in TNF-α production by peripheral blood mononuclear cells.

Example 8

The Sharp Decline in IL-10 (Interleukin 10) Production by Peripheral Blood Mononuclear Cells Following Treatment of an HIV-infected Patient Immediately after baseline blood sampling, the patient received apheresis; one apheresis per week, at a flow rate of 30 ml per minute, duration of each apheresis was 60 minutes. The sharp decline in IL-10 (interleukin 10) production by peripheral blood mononuclear cells following apheresis with the G-1 column is shown in FIG. 10. The production of IL-10 by peripheral blood mononuclear cells (PBMC) was measured by culturing $3\times10^6$ PBMC per well in 24-well LINBRO plates (Flow laboratories, Inc.) at 37° C. in a moist, 7% $CO_2$ atmosphere. The PBMC were then unstimulated or stimulated with PHA (M form, Grand Island, N.Y.) at a dilution 1:100. The supernatant was harvested after 48 hours of culture and cytokine production was then evaluated with a commercially available ELISA assay (Genzyme, Cambridge, Mass.).

IL-10 a major pathological factor in HIV-infection disease. IL-10 is a potent immune suppressor. It suppresses cytokine production by macrophages and thus indirectly suppresses T-cell activation. This counteracts the actions of IL-2 and IL-12 on cell-mediated immunity and IL-10 therefore effectively shuts down the immune system.

Example 9

The Change in HIV-1 DNA in Two HIV Patients and Disease-matched Controls

Two pairs of HIV patients were matched within each pair for disease state (A and B). Control patients were treated with HAART only, whilst G-1 patients were treated with HAART and with apheresis. Baseline was the level of HIV-1 DNA at the start of the study before apheresis treatment was commenced. Immediately after blood sampling, the G-1 patients received apheresis; one apheresis per week at a flow rate of 30 ml per minute, duration of each apheresis was 60 minutes. The change in HIV-1 DNA over the 8 weeks of treatment is shown in FIG. 11. The HIV-1 DNA falls sharply in the patients who received apheresis, but not in the patients treated with HAART alone. The HIV-1 DNA was measured as decribed in Example 1.

The Following additional, non-limiting Example 10 further illustrates the invention. Example 10 describes a preliminary investigation into the method and apparatus of the invention. Examples 1 to 9 relate to subsequent and more thorough investigations.

Example 10

The Changes in Viral Load, CD4-positive Cells, CD3+ Cells, CD4+CD28+ cells, CD4+CD45RA+ cells and CD4+CD25+ Cells in Two HIV Infected Patients Undergoing Apheresis Treatment As a blood treatment apparatus for the treatment of an HIV-infected disease, an external circulation apparatus composed in combination of a direct haemoperfusion column (capacity: about 335 ml) packed with cellulose acetate beads (220 g; diameter: 2 mm) and an adsorption-type haemocathartic apparatus ("ADAMONITOR MM6-P", tradename; manufactured by Otsuka Denshi K.K.) was used [clinical Study on Use of Granulocyte-Removing Apparatus (G-1) for Chronic Rheumatism", Ensho (Inflammation), 17(1), 57–80 (1997)].

The results of clinical tests on the above-described external circulation apparatus, said results being to be described subsequently herein, are a part of the results of a phase II study which was conducted following legitimate procedures in Italy (A PHASE II SAFETY AND EFFICACY EVALUATION OF COMBINED ANTI-RETROVIRAL DRUGS AND G-1 COLUMN: A PILOT STUDY).

From patients under treatment with an anti-retroviral (ARV) preparation composed in combination of two nucleoside reverse transcriptase inhibitors and one protease inhibitor, HIV-infected patients were chosen as subjects for treatment in accordance with the following standard: patients remaining under stable conditions over at least four months and generally one year owing to the ARV chemotherapy, having CD4-positive cell numbers not increased by 10% or greater from the corresponding base lines (the corresponding values before the initiation of the ARV therapy led to the stable conditions)(immunologically ARV-nonresponsive patients), and having more than 50,000 copies of HIV-RNA or showing a decrease in HIV-RNA not greater than 0.5 log ($\leq 0.5$ log) since the beginning of HAART owing to the ARV chemotherapy led to the stable conditions (virologically ARV-nonresponsive patients).

The treatment of the HIV-infected disease by the external circulation apparatus according to the present invention was conducted in substantially the same manner as in the clinical study on chronic rheumatism as described in the report referred to in the above. The treatment was conducted once a week by setting the amount of blood, which is to be circulated externally per treatment, on the basis of a blood flow rate of 30 ml/minute and an external circulation time of 60 minutes as standards.

The results of the treatment of Patient 1 (48 years old, male) and Patient 2 (43 years old, male) are shown in Table 3.

The test items in Table 3 were all measured by methods commonly employed in the art, and include the number of white blood cells (WBC), the number of neutrophils, the number of monocytes, the number of eosinophils, the number of lymphocytes, the numbers of lymphocyte surface markers, the number of hemoglobins, the number of platelets, and the viral load.

Specifically, the number of each lymphocyte surface marker was determined as a result of a measurement by flow cytometry while making use of a monoclonal antibody of the marker. "CD3" indicates the number of CD3-positive cells, "#CD4" the number of CD4-positive cells, "% CD4" the percentage of the CD4-positive cells based on lymphocytes, "CD4/8" the ratio of the CD4-positive cells to CD8-positive cells, "CD4+CD45RA+" the percentage of CD45RA-positive cells based on the CD4-positive cells, "CD4_CD25+(IL-2)" the percentage of CD25-positive cells based on the CD4-positive cells, and "CD4+CD28+(Th-1)" the percentage of CD28-positive cells based on the CD4-positive cells.

Further each viral load is determined as a result of a measurement of a serum level of HIV-RNA by the RT-PCR method (cp: the number of copies per ml).

Based on the results shown in Table 3 and Table 4, the rates (%) of increases in the number of CD4-positive cells from the respective base lines and the variations in viral load (the number of copies) are shown in FIG. 12 (Patient 1) and FIG. 13 (Patient 2), respectively. Further, the variations in the percentage of CD3-positive cells based on lymphocytes and the variations in "CD4+CD45RA+", CD4+CD25+(IL-2)" and "CD4+CD28+(th-1 are shown in FIG. 14 (Patient 1: dots, Patient 2: circles).

Concerning Patient 1 and Patient 2, increases (50 to 70%) in the number of CD4-positive lymphcytes were already observed after the treatment by the present invention (as early as 60 minutes after the initiation), and this effect lasted for 3 to 7 days or even longer. In addition, by conducting the second therapy (treatment), this effect was observed to last for 7 days or longer in both of the patients.

TABLE 3

|  | Patient 1 | | | | |
| --- | --- | --- | --- | --- | --- |
|  | 1st apheresis | | 3 days | 2nd apheresis | |
|  | Baseline | 60 min | later | Baseline | 60 min |
| Number of WBC |  |  |  | 5,300 | 4,200 |
| Number of neurophils | 2,300 | 2,500 | 2,800 | 2,900 | 2,400 |
| Number of monocytes | 500 | 300 | 200 | 700 | 400 |
| Number of eosinophils | 20 | 10 | 20 |  |  |
| Number of lymphocytes | 1,600 | 1,100 | 1,500 | 1,600 | 1,300 |
| CD3 | 791 | 1,179 | 1,130 |  |  |
| #CD4 | 219 | 323 | 365 | 234 | 333 |
| % CD4 | 19.9 | 20.2 | 24.3 | 19.6 | 22.7 |
| CD4/8 | 0.45 | 0.44 | 0.53 | 0.40 | 0.50 |
| CD4+CD45RA+ | 0.60 | 13.10 |  |  |  |
| CD4+CD25+ (IL-2) | 10.2 | 18.02 |  |  |  |
| CD4+CD28+ (Th-1) | 7.00 | 16.30 |  |  |  |
| Number of hemoglobins | 14.2 | 13.5 | 14.0 | 14.6 | 13.8 |

TABLE 3-continued

| | Patient 1 | | | | |
| --- | --- | --- | --- | --- | --- |
| | 1st apheresis | | 3 days later | 2nd apheresis | |
| | Baseline | 60 min | | Baseline | 60 min |
| Number of platelets | 130 | 124 | 127 | 143 | 129 |
| Viral load | 89,000 cp | 20,000 cp | | | |

TABLE 4

| | Patient 2 | | | | |
| --- | --- | --- | --- | --- | --- |
| | 1st apheresis | | | 2nd apheresis | |
| | Baseline | 60 min | 75 min | Baseline | 60 min |
| Number of WBC | | | | 6,000 | 5,000 |
| Number of neurophils | 2,400 | 2,300 | 2,500 | 1,700 | 2,000 |
| Number of monocytes | 700 | 600 | 500 | 700 | 500 |
| Number of eosinophils | 30 | 10 | 0 | | |
| Number of lymphocytes | 1,800 | 2,600 | 2,500 | 3,300 | 2,200 |
| CD3 | 1,541 | 2,213 | 2,078 | | |
| #CD4 | 284 | 478 | 488 | 468 | 451 |
| % CD4 | 15.0 | 18.0 | 19.5 | 14.0 | 20.0 |
| CD4/8 | 0.24 | 0.29 | 0.33 | | |
| CD4+CD45RA+ | 4.10 | 5.40 | | | |
| CD4+CD25+ (IL-2) | 12.02 | 19.02 | | | |
| CD4+CD28+ (Th-1) | 8.60 | 12.90 | | | |
| Number of hemoglobins | 13.4 | 12.7 | 12.6 | 14.8 | 13.6 |
| Number of platelets | 187 | 169 | 166 | 253 | 194 |
| Viral load | 31,000 cp | | | 26,000 cp | |

These prompt increases in the number of CD4-positive lymphocytes are postulated to be attributable to recovery and enhancement of myeloid function by the treatment in accordance with the present invention and formation of new CD3-positive cells, especially a group of naive cells such as CD45RA-positive cells, CD25-positive cells and CD28-positive cells, as shown in FIG. 14. Such an increase is an outcome not observed at all from the conventional methods for the treatment of HIV-infected diseases. In addition, the treatment method according to the present invention has been recognised to bring about a decrease in viral load and hence to enhance its effect.

REFERENCES

1. Lazarus H. M. et al. Selective in vivo removal of rheumatoid factor by an extracorporeal treatment device in rheumatoid arthritis patients. Transfusion, 1991; 31: 122–128.
2. Eshleman J. R. and Silberstein L. E. The development of selective plasmapheresis as a means for specific therapeutic intervention (editorial). Transfusion, 1991; 31: 96–98.
3. Fauci A S. Host factors and the pathogenesis of HIV-induced disease. Nature, 1996; 384: 529–533.
4. Cassone A., et al. (1997). Possible participation of polymorphonuclear cells stimulated by microbial immunomodulators in the dysregulated cytokine patterns of AIDS patients. J. Leukoc. Biol., 1997 62: 60–66.
5. Richman D D. HIV therapeutics. Science 1996; 272:1886–1888.
6. Saag M S. et al. HIV viral load markers in clinical practice. Nature Med. 1996; 2:625–629.
7. Oyaizu N and Pahwa S. Role of apoptosis in HIV disease pathogenesis. J. Clin. Immunol. 1995; 15:27–231.
8. Briant L. Binding of HIV-1 virions or gp120 anti-gp120 immune complexes to HIV-1 infected quiescent peripheral blood mononuclear cells reveals latent infection. J. Immunol. 1996; 156: 3994–4004.
9. Herbein G. et al. Apoptosis of CD8 T cells is mediated by macrophages through interaction of HIV gp120 with chemokine receptor CXCR4. Nature 1998; 395, 189–194.
10. Clerici, M and Shearer, G. M. A TH1→TH2 switch is a critical step in the aetiology of HIV infection. Immunol Today 1993;14:107–111.
11. Clerici, M and Shearer, G. M (1994a) The TH1/TH2 hypothesis of HIV infection: new insights. Immunol Today 1994; 15:575–581.
12. Chehimi J. et al. IL-12 deficiency in HIV-infected patients. J. Exp. Med. 1994; 179: 1361–1366.
13. Connors M et al. HIV infection induces changes in the CD4 T cell phenotype and depletions within the CD4 T cell repertoire that are not immediately restored by antiviral or immune based therapies. Nature Med, 3:533–540, 1997.
14. Pakker N G. et al. Patterns of T cell repopulation, viral load reduction, and restoration of T cell function in HIV-infected persons during therapy with different anti-retroviral agents. J AIDS Hum Retrovir 1997; 16:318–326.

15. Angel J B. et al. Improvement in cell-mediated immune function, during potent anti-human immunodeficiency virus therapy with ritonavir plus saquinavir. J Inf Dis 1998; 177:808–904.
16. de Jong M D. et al. Summary of the international consensus symposium on management of HIV, CMV and hepatitis virus infections. Antiviral Res. 1998; 37:1–16.
17. Oyaizu N. et al. Accelerated apoptosis in PBMC from human immunodeficiency infected patients and in CD4 cross-linked PBMC from normal individuals. Blood 1993; 82:3392–3400.
18. D'Arrigo C., et al. Human neutrophil Fc receptor-mediated adhesion under flow: a hollow fiber model of intravascular arrest. Clin. Exp. Immunol., 1995; 100: 173–179.

What is claimed is:

1. A method of treatment of a subject infected with a pathogenic organism comprising contacting blood from said subject with an adsorbent carrier whereby infected, activated or defective lymphocytes are adsorbed, and returning activated or defective lymphocytes are adsorbed, and returning the resulting blood to said subject, wherein said adsorbent carrier has a contact angle to water of from 55° to 95°.

2. The method of claim 1, wherein said pathogenic organism is a virus.

3. The method of claim 2, where said virus is HIV.

4. The method of claim 2, where said virus is HCV.

5. The method of claim 1, wherein said pathogenic organism is an intracellular pathogenic organism.

6. The method of claim 5, wherein said intracellular pathogenic organism is *Mycobacterium leprae.*

7. The method of claim 1, wherein said adsorbent carrier is selected from the group consisting of polystyrene, cellulose acetate, nylon, polytrifluoroethylene and polyethylene terephthalate.

8. The method of claim 7, wherein said adsorbent carrier is cellulose acetate.

9. The method of claim 1, wherein said adsorbent carrier is in the form of beads.

10. The method of claim 9, wherein said beads have a diameter of from 0.1 to 10.0 mm.

11. The method of claim 10, wherein said beads have a diameter of from 0.2 to 5.0 mm.

12. The method of claim 11, wherein said beads have a diameter of from 0.5 to 4.0 mm.

13. The method of claim 12, wherein said beads have a diameter of from 1.0 to 3.0 mm.

14. The method of claim 1, wherein said adsorbent carrier has a roughened surface.

15. The method of claim 14, wherein said adsorbent carrier has on its surface irregularities having a center line average height (Ra), as defined under Japanese and Industrial Standard BO601-1982, of from 0.2 µm to 10 µm, and a mean spacing (Sm) of unevenness of from 5 µm to 200 µm.

16. The method of claim 1, wherein said adsorbent carrier comprises cellulose acetate beads having a diameter of from 0.1 to 10.0 mm.

17. A method of treatment of a subject afflicted with a disease or disorder in which lymphocytes are infected, activated or defective comprising contacting blood from said subject with an adsorbent carrier and returning the resulting blood to said subject, wherein said adsorbent carrier has a greater affinity for infected, activated or defective lymphocytes than for uninfected, non-activated or non-defective lymphocytes, respectively, so as to remove said infected, activated or defective lymphocytes from said blood.

18. The method of claim 17, wherein said adsorbent carrier has a greater affinity for infected or activated lymphocytes than for uninfected or non-activated lymphocytes respectively.

19. The method of claim 18, wherein said adsorbent carrier has a greater affinity for infected lymphocytes-than for uninfected lymphocytes.

20. The method of claim 17, wherein said disease or disorder is caused by a virus.

21. The method of claim 20, where said virus is HIV.

22. The method of claim 20, where said virus is HCV.

23. The method of claim 17, wherein said disease or disorder is caused by an intracellular pathogenic organism.

24. The method of claim 23, wherein said intracellular pathogenic organism is *Mycobacterium leprae.*

25. The method of claim 17, wherein said lymphocytes are $CD4^+$ lymphocytes.

26. The method of claim 17, wherein said adsorbent carrier has a contact angle to water of from 55° to 95°.

27. The method of claim 26, wherein said adsorbent carrier is selected from the group consisting of polystyrene, cellulose acetate, nylon, polytrifluoroethylene and polyethylene terephthalate.

28. The method of claim 27, wherein said adsorbent carrier is cellulose acetate.

29. The method of claim 17, wherein said adsorbent carrier is in the form of beads.

30. The method of claim 29, wherein said beads have a diameter of from 0.1 to 10.0 mm.

31. The method of claim 30, wherein said beads have a diameter of from 0.2 to 5.0 mm.

32. The method of claim 31, wherein said beads have a diameter of from 0.5 to 4.0 mm.

33. The method of claim 32, wherein said beads have a diameter of from 1.0 to 3.0 mm.

34. The method of claim 17, wherein said adsorbent carrier has a roughened surface.

35. The method claim 34, wherein said adsorbent carrier has on its surface irregularities having a center line average height (Ra), as defined under Japanese and Industrial Standard BO601-1982, of from 0.2 µm to 10 µm, and a mean spacing (Sm) of unevenness of from 5 µm to 200 µm.

36. The method of claim 17, wherein said adsorbent carrier comprises cellulose acetate a diameter of from 0.1 to 10.0 mm.

* * * * *